United States Patent
Chandler (10) Patent No.: US 8,398,647 B2
(45) Date of Patent: Mar. 19, 2013

(54) SURGICAL INSTRUMENT

(75) Inventor: Matt Chandler, Preston (GB)

(73) Assignee: Depuy International Limited (GB)

( * ) Notice: Subject to any disclaimer, the term of this patent is extended or adjusted under 35 U.S.C. 154(b) by 781 days.

(21) Appl. No.: 12/390,071

(22) Filed: Feb. 20, 2009

(65) Prior Publication Data
US 2009/0209966 A1    Aug. 20, 2009

(30) Foreign Application Priority Data
Feb. 20, 2008 (GB) .................................. 0803041.3

(51) Int. Cl.
*A61B 17/58* (2006.01)
(52) U.S. Cl. .......................................................... 606/92
(58) Field of Classification Search .............. 606/92–94, 606/86, 89; 623/23.12–23.14, 23.19, 23.2
See application file for complete search history.

(56) References Cited

U.S. PATENT DOCUMENTS

| 4,896,663 A * | 1/1990 | Vandewalls ...................... 606/79 |
| 6,156,069 A | 12/2000 | Amstutz |
| 2005/0245936 A1 * | 11/2005 | Tuke et al. ....................... 606/89 |
| 2006/0004375 A1 * | 1/2006 | Watkins et al. ................... 606/94 |
| 2007/0162038 A1 * | 7/2007 | Tuke ............................... 606/88 |

FOREIGN PATENT DOCUMENTS

| DE | 202005015667 U1 | 1/2006 |
| EP | 1316297 A1 | 6/2003 |
| GB | 2384992 A | 8/2003 |
| WO | 2004032767 A1 | 4/2004 |
| WO | 2006054062 A1 | 5/2006 |
| WO | 2008092788 A1 | 8/2008 |

OTHER PUBLICATIONS

Eska Implants GmbH; German Patent No. DE202005015667U1; Jan. 12, 2006; English Abstract; MicroPatent Report; 2009 MicroPatent LLC.
EP Search Report EP09152887 dated Jun. 18, 2009.

* cited by examiner

*Primary Examiner* — Kevin T Truong
*Assistant Examiner* — Melissa A Hall (57) ABSTRACT

An instrument is provided for controlling the distribution of bone cement on a surface of a prepared bone so as to prepare the bone to receive a resurfacing prosthesis. The instrument includes a shaft having a shaft axis configured to at least partially disposed within the bore of the bone, and at least one arm coupled to the shaft. The at least one arm is configured to rotate about the shaft axis and shaped so as to contact the cement on the bone when the at least one arm is rotated about the shaft axis.

15 Claims, 6 Drawing Sheets

SURGICAL INSTRUMENT

FIELD OF THE INVENTION

The present invention relates to an instrument for controlling the distribution of bone cement on the surface of the head of a bone to prepare the head of the bone to receive a re-surfacing prosthesis. In particular, but not exclusively, the present invention relates to an instrument for controlling the distribution of bone cement on the surface of the head of a bone which provides the ball component of a ball and socket joint, to prepare the head of the bone to receive a re-surfacing prosthesis.

BACKGROUND OF THE INVENTION

When ball and socket joints such as hip joints and shoulder joints are damaged, it is common to replace the entire joint with a joint prosthesis. In the case of a damaged hip joint, replacement involves resection of the proximal femur and implantation of the femoral component of an orthopedic joint, which includes a stem part which can be received in the intramedullary canal, and a head part with a convex bearing surface. The patient's acetabulum is prepared to receive the acetabular component of the joint prosthesis, which provides a concave bearing surface to articulate with the bearing surface on the femoral component. Frequently, bone cement is used to affix the components of the prosthesis within their respective prepared bone cavities.

When the condition of the femoral bone tissue is generally good, it can be desirable to retain much of the proximal femur. Accordingly, techniques have been developed in which the femoral head is fitted within a hollow resurfacing shell. The resurfacing shell has a convex outer surface which is highly polished which enables it to act against the hollow bearing surface of an acetabular component. Such techniques are referred to as Articular Surface Replacement techniques. They have the advantage that the quantity of bone which has to be removed from the head of the bone is only small. A tool which can be used to prepare the head in this way is disclosed in WO-2004/032767.

A bone cement can be used to ensure that an appropriate bond is formed between a resurfacing shell and the prepared head of a femur or other bone. Certain known techniques involve the use of cements having relatively low viscosities, and the techniques involve providing a quantity of the cement within the resurfacing shell, which is then fitted on to the prepared head. Reception of the head within the shell causes the cement to be displaced. Alternatively, the bone cement is applied to the head of the bone prior to the fixation of the implant. The use of low viscosity bone cements enables good penetration of the cancellous bone and ensures that the cement can be displaced when the shell was fitted on to the head of the bone, so that the shell can be properly seated.

The use of low viscosity bone cement for fixing a re-surfacing implant has a number of disadvantages. These include that the low viscosity cement has to be mixed and applied to the prepared head of a bone in a very short time period, as it has been found that such cements typically take only 20 minutes to set after mixing. The surgical team is therefore placed under pressure and the flexibility of the technique is limited. Low viscosity bone cement has the further disadvantage that once the cement has been applied to the head of the bone the implant must be carefully held in place until the bone cement has set. Furthermore, it has been found that the pressurisation of low viscosity cement is difficult to sustain and control. This lack of control can sometimes lead to inadequate fixation of the bone cement to the head of the bone.

The use of low viscosity cements in the fixation of articular surface prosthesis components has been found to promote a high degree of penetration of the cement into the bone beneath the pole of the implant, but with a progressive reduction in the degree of penetration of the cement towards the periphery of the implant. This variation in the degree of the penetration of the cement into the bone at the head of the bone can lead to a number of problems. Firstly, if there is a high mass of bone cement in the region of the pole of the implant this may lead to an increased temperature in the bone cement during the setting period, which may give rise to elevated bone necrosis in the region of the pole of the implant. Additionally, an excess of bone cement in the polar region of the head of the bone can in some circumstances prevent the re-surfacing prosthesis from being properly seated on the head of the bone when the re-surfacing prosthesis is fitted. Furthermore a lower degree of penetration of the cement into the bone at the periphery of the implant will result in a lower level of fixation of the implant and therefore a lower torsional stability of the implant. Finally, if there is a low degree of adhesion of the bone cement at the implant/bone interface then the peripheral region will also be open to ingress by foreign particles.

Commonly, a re-surfacing shell has a stem extending along the polar axis, which is received in a bore in the head of the bone along the polar axis of the head. It has been found that cementing techniques employing low viscosity cements have the further disadvantage that, when the re-surfacing implant is fitted, the bone cement is drawn down with the stem of the implant during insertion. This displacement of the bone cement potentially leads to a more secure fixation of the stem of the implant than the implant itself. This has an additional clinical disadvantage of stress shielding which could result in a subsequent loss of bone adjacent to the implant underside.

It has therefore been found to be desirable to use high viscosity cements. However, cementing techniques employing low viscosity cements cannot be used with high viscosity bone cements as the forces required to extrude the excess bone cement of high viscosity from the head of a bone have been found to be too large. This has made it difficult for such techniques to provide a uniform distribution of high viscosity bone cement on the surface of the head of the bone, so that the correct seating of the implant can be difficult to achieve.

Accordingly, alternative techniques were required to be developed for use with high viscosity cements. One such technique is disclosed in WO-2006/054062. While the technique disclosed in WO-2006/054062 provides an effective means for controlling the distribution of bone cement on the surface of the head of a bone to prepare the head of the bone to receive a re-surfacing prosthesis, it has been found to be desirable to develop further alternative techniques suitable for use with high viscosity cements.

SUMMARY OF THE INVENTION

According to a first aspect of the present invention, an instrument is provided for controlling the distribution of bone cement on a surface of a prepared bone so as to prepare the bone to receive a resurfacing prosthesis. The instrument includes a shaft having a shaft axis configured to at least partially disposed within the bore of the bone, and at least one arm coupled to the shaft. The at least one arm is configured to rotate about the shaft axis and shaped so as to contact the cement on the bone when the at least one arm is rotated about the shaft axis.

It will be understood that the head of the bone is prepared in that it has been shaped in preparation for receiving the re-surfacing prosthesis. As is known in re-surfacing techniques of the kind with which this invention is concerned, shaping the bone can involve removing bone from the surface of the head of the bone, for example to create two conical portions. The included angle of the conical surface which extends from the pole of the head has a greater included angle than the surface of the truncated cone which is spaced from the pole and which faces generally away from the bone head. For example the included angle of the conical surface which extends from the pole of the head might be in the range from about 90° to about 170°. The included angle of the conical surface which is spaced from the pole and which faces generally away from the bone head might be in the range from about 3° to about 30°.

instrument of the invention can enable the distribution of bone cement on the surface of a head of a bone to be controlled. For example, it can control the thickness of the layer of cement on the surface of the bone which faces generally along the axis of the relevant portion of the bone (which is the axis of the head, for example the femoral neck axis in the case of an instrument for use in preparing a femur to receive the femoral component of a hip joint prosthesis). Control of the thickness of the bone cement in this region can be important to ensure that a resurfacing prosthesis component is properly seated on the bone. It has been found that failure to control the thickness of a cement mantle in this region can lead to fractures in the neck region due to improper seating of the joint prosthesis component. The advantages that are available from the present invention in helping to address this problem are therefore significant.

The instrument of the invention may help to ensure that an adequate layer of bone cement is provided on the surfaces of the bone which face generally away from the axis of the bone. In particular, the contact between the at least one arm and cement on the bone can help to force the cement into the porous structure of the bone, which may be the porous structure of cancellous bone, and which can be desirable to achieve adequate fixation. The instrument can also help to control the thickness of the cement mantle on the surfaces of the bone which face away from the axis of the bone. This can help to provide secure fixation between the bone and the internal surfaces of a hollow prosthesis component, close to the open edge of the component, which can provide an important contribution to fixation of a prosthesis component on the bone so that twisting forces can be resisted. The thickness of the mantle of cement which is provided on the surface of the bone, especially the surfaces of the bone which face generally away from the bone axis, may then be controlled by the clearance between the at least one arm and the surface of the bone.

In use, the instrument may be fitted on to the head of a bone which has been pre-coated with a bone cement, especially with a bone cement whose viscosity is such that it does not tend to flow freely from the bone after application. The arm is then rotated, preferably in a single direction, contacting bone cement on the head of the bone in a sweeping action. Excess bone cement on the head of the bone can be displaced by the arm as it sweeps over the cement mantle on the head of the bone.

The arm can be used to apply pressure as it is rotated to a cement mantle formed on the head of the bone more uniformly than if a resurfacing head itself is relied on to apply the pressure, while being positioned on the head of the bone. This can enable penetration of the cement into the porous structure of the bone to be more uniform, including into surfaces of the bone which face generally radially outwardly relative to the polar axis of the head of the bone as well as into the surfaces around the pole. This can enable the interface between the bone and the resurfacing shell to withstand torsional forces more effectively. It can provide greater resistance to ingress of foreign particles at the interface between the head of the bone and the implant at its periphery. It can also provide a more uniform distribution of bone cement around the head of the bone; in particular, the tendency for cement to collect at the pole can be reduced. This therefore reduces the risk of localised accumulation of bone cement which may lead to a higher than normal temperature as the cement cures, possibly leading to damage of the bone tissue in some circumstances.

The instrument of the invention can be used with high viscosity bone cements which do not flow readily. Such bone cements typically have a dough like consistency and are substantially self-supporting so that a quantity of the cement does not flow significantly when left to stand for a period of about 10 minutes. This allows a cement to be manipulated when used in a surgical procedure, after it has been mixed. Such a cement can be applied to the head of a bone manually, for example by finger packing or by use of a syringe system. The advantage of using a syringe system is that this provides a 'no touch' method of application of the bone cement. Generally, the viscosity of a high viscosity cement, before application to the surface of the bone, will be at least about $10^6$ cp, preferably at least about 1.5 H $10^6$ cp.

The arm is rotated when the instrument is in use around an axis which is defined by the shaft. The axis which is defined by the shaft will generally be aligned with the axis of the head of the bone. For example, when the bone is a femur, the axis which is defined by the shaft will be aligned approximately with the axis of the femoral neck. Techniques for establishing the axis of the femoral neck are known.

The at least one arm may be shaped to define a space between an internal surface thereof and the surface of the head of the bone. The dimensions of the space will determine the amount of cement left on the head following rotation of the arm about the head.

Optionally, the shaft can be releasably mounted relative to the bone, and can be located extending from the head of the bone. The shaft can be mounted by arranging the shaft to be a tight, interference fit within an axially extending cavity in the bone, or may be mounted using a separate securing member. The bore in a bone will frequently have approximately parallel sides such as might be formed by drilling. Accordingly, it will generally be preferred that the portion of a shaft which is to be received in a bore in a bone has an approximately constant cross-section, especially a circular cross-section.

Preferably, the instrument includes a formation which limits the depth to which the shaft can be inserted into a bore in the bone. For example, this might comprise a collar or other fitting which extends transversely from the side wall of the shaft.

The at least one arm may be rotatably mounted on the shaft, to thereby permit rotation of the arm about the head of the bone. Securing the shaft to the bone may permit accurate location of the arm with respect to the head of the bone, so as to enable an effective and accurate distribution of cement on the surface of the head of the bone. The at least one arm may be coupled to the shaft by means of a coupling. For example, the arm can be journalled to the shaft using a bearing or the like.

The shaft can be rotatably mounted relative to the bone such that the shaft with the arm is rotated relative to the head of the bone.

Optionally, the arm can be releasably coupled to the shaft, which may permit one or more arms of different shape(s) and/or dimension(s) to be used with the shaft. Providing an instrument in which a number of such different arms may be used may facilitate use of the instrument in controlling the distribution of cement on the surfaces of heads of bones prepared to different shapes/dimensions.

The arm may comprise a plurality of arm portions. Each of the arm portions may be approximately straight. A first arm portion may extend from the shaft to a second arm portion, and at least part of said first arm portion may be disposed inclined relative to another part of said first arm portion and/or the shaft. The second arm portion may extend from an end of the first arm portion which end may be remote from the shaft.

The angle between the shaft and the first arm portion may be at least about 30°, and may be at least about 45°. The angle between the shaft and the first arm portion may be no more than about 85°. The angle between the shaft and the first arm portion may be between about 45° and about 85°.

The angle between the second arm portion and a line which is parallel to the shaft (and which may be a main axis of the shaft) may be at least about 3°, and may be at least about 5°. The angle between the second arm portion and a line which is parallel to the shaft may be no more than about 15°. The angle between the second arm portion and a line which is parallel to the shaft may be between about 3° and about 15°.

The arm portions might be separable. The arm portions will generally be rigidly connected to one another so that the angle between them does not change significantly when the arm is rotated about the prepared head of the bone.

A length of the first arm portion may be at least about 2 cm, and may be at least about 3 cm. A length of the first arm portion may be no more than about 5 cm, and may be no more than about 4 cm.

A distance between an internal surface of the second arm portion and a line which is parallel to the shaft (typically a main axis of the shaft) may be at least about 1.25 cm, may be at least about 1.5 cm, may be at least about 2 cm, or may be at least about 2.5 cm. Said distance may be no more than about 3 cm. A ratio of said distance relative to a corresponding radius (centred on said line) of the prepared head of the bone may be in the range 1.05:1 to 1.2:1.

The angle between the first arm portion and the shaft, and/or the length of the first arm portion, may be the main factors which dictate the dimensions of a path described by the arm when the arm is rotated about the head of the bone, and thus the dimension of a prepared bone with which the instrument can be used (at least where the angle between the second arm portion and a line which is parallel to the shaft is relatively small, say between about 3° and about 15°).

The shaft may comprise a first portion which can be releasably mounted relative to the bone and a second portion secured to the at least one arm, the second portion being rotatable relative to the first portion, such as through a rotatable coupling or joint. In this fashion, the at least one arm may be rotated about the head by rotating the second portion of the shaft, carrying the arm, relative to the first portion.

The arm may comprise a support portion and at least one wiper portion mounted on or coupled to the support portion, the wiper portion adapted to contact the cement on the head of the bone in use of the instrument. The wiper portion may be of a material having a lower hardness and/or which is more flexible than a material of the support portion. Use of a wiper portion which is formed from a resilient material can facilitate the application of a force to a cement mantle on the surface of a prepared head of a bone, so that the cement is forced into the porous structure of the bone. The wiper portion may be formed from a flexible polymeric material. Suitable materials include certain polyolefins, especially polyethylenes, polypropylenes and copolymers thereof, and certain silicone rubbers. The material of the wiper portion should be selected so that said portion is sufficiently stiff to be able to displace bone cement material as the instrument is rotated on the head of the bone. A suitable material will generally have a Shore hardness of not more than about 100, preferably not more than about 80, for example not more than about 70. A suitable material will generally have a Shore hardness of at least about 10, preferably at least about 15, more preferably at least about 25, and may have a Shore hardness of 10, 15, 20, 40 or 60.

When the arm comprises more than one arm portion, a wiper portion can be provided on one or more of the arm portions.

Preferably, the part of the arm which is directed towards the prepared surface of the head of the bone is inclined to that surface when the instrument is in use. The inclined arrangement of the arm can be achieved as a result of flexing of the material of the arm (especially the wiper portion of the arm) when the arm is rotated about the head of the bone. Preferably, the angle between the arm at the edge which contacts the cement mantle and the radius extending from an axis of the shaft is at least about 10°, more preferably at least about 20°, especially at least about 30°, for example about 45°. An inclined edge can be used to apply force to the cement mantle, to force cement into the porous structure of the prepared bone head.

The instrument can have more than one arm. Two or more arms can be coupled together or otherwise associated so that the arms are moved together relative to the head of the bone. The arms may be independently movable.

The instrument may comprise a depth stop, which may be provided on the shaft, for restricting passage of the shaft into a cavity in the head of the bone. This may facilitate accurate location of the arm relative to the head of the bone and thus control of a spacing between an internal surface of the at least one arm and an external surface of the head, and thereby a thickness of a cement mantle formed thereon.

The at least one arm may be rotatable and/or axially movable relative to the shaft. Providing an at least one arm which is axially movable on the shaft may facilitate variation of the thickness of the cement mantle formed and/or may assist in urging cement into the porous structure of the bone. The at least one arm may be biased, in use, in a direction away from the head of the bone, and the instrument may comprise a spring which can exert a biasing force on said arm. Where the instrument comprises a depth stop, the spring may be positioned between the depth stop and said arm, and may be arranged to exert a biasing force on a base portion of said arm or on a base portion of an arm assembly comprising said arm.

The instrument may comprise a handle which may be secured against rotation relative to the shaft and which may be provided on an end of the shaft, or the handle may be rotatable about the shaft. Where the handle is rotatable about the shaft, the handle may be secured to the at least one arm for rotation with the arm relative to the shaft. Accordingly, said arm may be rotated about the head of the bone by rotating the handle relative to the shaft.

The head of the bone may be prepared using a reamer. A tool which can be used to prepare the head in this way is disclosed in WO-2004/032767.

The viscosity of a bone cement can be measured using a viscometer. An example of a suitable instrument is that available under the trade name Brookfield RVDV-III. The reactive bone cement components (generally a powder and a liquid) should be at 23 EC before mixing, and should be thoroughly mixed (in line with manufacturer's instructions) before the viscosity measurements are taken.

According to a second aspect of the present invention, there is provided apparatus for use in the resurfacing of the head of a bone which provides the ball component of a ball and socket joint, the apparatus comprising an instrument according to the first aspect of the invention and a quantity of a bone cement.

Preferably, the viscosity of the cement, after mixing and before application to the surface of the bone, is at least about $10^6$ cp.

Preferably, the apparatus includes a resurfacing shell which has a polished external surface which can function as a bearing surface, and which defines an internal cavity in which the head of the bone can be received.

According to a third aspect of the present invention, there is provided apparatus for use in the resurfacing of the head of a bone which provides the ball component of a ball and socket joint, the apparatus comprising an instrument according to the first aspect of the invention and a resurfacing shell.

The resurfacing shell may have a polished external surface which can function as a bearing surface, and which defines an internal cavity in which the head of the bone can be received. The at least one arm may be shaped to define a layer of bone cement on the head of the bone, in use of the instrument, of a shape corresponding to that of the internal cavity of the resurfacing shell.

Preferably, the instrument is designed so that a mantle of cement is formed on the surface of the head of the bone which is at least about 0.5 mm thick, more preferably at least about 0.75 mm thick. Preferably, the instrument is designed so that the thickness of the mantle is not more than about 2.0 mm, more preferably not more than about 1.5 mm, especially not more than about 1.25 mm.

Preferably, the shape of the cement mantle which is created by rotation of the arm about the head of the bone is such that the cement mantle is compressed slightly when the resurfacing shell is fitted to the bone with the cement mantle on it. This can be achieved by arranging for the cement mantle to be slightly bigger than the cavity within the resurfacing shell. Consequently, when the shell is fitted to the prepared head of the bone, with the cement mantle on it, the cement is forced into the porous structure of the bone, and some cement might be displaced from within the shell. Preferably, the difference between the diameter of the cement mantle and the diameter of the cavity within the shell at a point which is half way between the opening to the cavity and the pole is at least about 0.5 mm, more preferably at least about 1.0 mm. Preferably, the difference between these diameters is not more than about 2.0 mm.

According to a fourth aspect of the present invention, there is provided an instrument for controlling the distribution of bone cement on a surface of a prepared head of a bone to prepare the bone to receive a re-surfacing prosthesis, the instrument comprising:
 a shaft which can be coupled to the bone such that the shaft extends in a direction away from the head of the bone; and
 at least one arm coupled to the shaft, which arm can be rotated about the shaft and which arm is shaped so as to contact cement on the head of the bone in a sweeping action when said arm is rotated about the shaft.

According to a fifth aspect of the present invention, there is provided an instrument for controlling the distribution of bone cement on a surface of a prepared head of a bone to prepare the bone to receive a re-surfacing prosthesis, the instrument comprising:
 a shaft which can be coupled to the bone such that the shaft extends in a direction away from the head of the bone; and
 at least one arm extending from the shaft;
wherein the shaft can be rotated relative to the bone and wherein said arm is shaped such that when the shaft is rotated said arm contacts cement on the head of the bone in a sweeping action.

According to a sixth aspect of the present invention, there is provided a kit of parts to be assembled to form an instrument for controlling the distribution of bone cement on a surface of a prepared head of a bone to prepare the bone to receive a re-surfacing prosthesis, the instrument comprising:
 a shaft which can be coupled to the bone; and
 at least one arm which can be coupled to the shaft, which arm can be rotated about the head of the bone and which arm is shaped so as to contact cement on the head of the bone in a sweeping action when said arm is rotated about the head;
 wherein the at least one arm is selected from a group comprising a plurality of different arms.

Each arm may be of a different shape and/or dimension(s). Each arm may comprise a plurality of arm portions, and may comprise a first arm portion extending (in use) from the shaft to a second arm portion, the second arm portion extending from an end of the first arm portion remote from the shaft. An angle between the first arm portion and the shaft, and/or the length of the first arm portion, may be different in each arm of the group. An angle between the second arm portion and a line which is parallel to the shaft may be different in each arm of the group.

Further features of the shaft and/or at least one arm of the kit may be as described above in or with reference to the first to fifth aspects of the invention.

BRIEF DESCRIPTION OF THE DRAWINGS

An embodiment of the present invention will now be described, by way of example only, with reference to the accompanying drawings, in which.

DETAILED DESCRIPTION OF THE DRAWINGS

Figure 1:
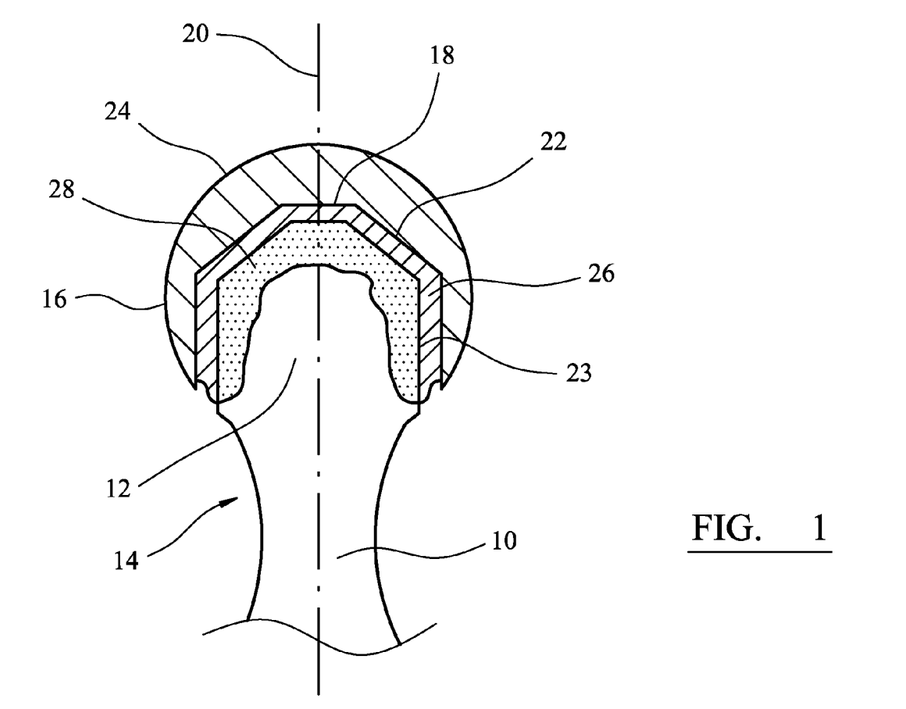
FIG. 1 is a cross-section through a femoral head which has had a resurfacing shell fitted to it.

Referring firstly to FIG. 1, there is shown a neck 10 and head 12 of a femur 14 to which a resurfacing shell 16 has been affixed using a high viscosity bone cement. It should be noted that whilst the present invention is described herein for use in relation to resurfacing of a femur, the present invention has utility in relation to bones other than the femur, including for example the humerus.

The head 12 of the femur 14 shown in FIG. 1 has previously been prepared to receive the resurfacing shell at 16 by reaming it to form a generally planar surface 18 facing along an axis 20 of the femoral neck 10 and head 12, a side surface 22 which is inclined to the axis 20 so that the angle between the side surface 22 and the axis 20 is about 45 1, and a side surface 23 which is typically tapered at an angle of around 3° relative to the axis 20. However, the side surfaces 22 and 23 may be disposed at alternative angles relative to the axis 20. For example, the side surface 23 may be disposed parallel to the axis 20.

The resurfacing shell 16 defines an internal cavity in which the head 12 of the femur 14 is fitted. The shape of the cavity corresponds to the shape of the reamed head 12 but it is sized so that there is a gap between it and the surface of the bone which is about 1 mm thick. The resurfacing shell 16 has an external surface 24 which is polished as is known, to provide a bearing surface which can articulate with a corresponding bearing surface of an acetabular component.

A mantle of a high viscosity bone cement 26 such as that sold by DePuy CMW under the trade mark SmartSet GHV is provided between the surface of the bone and the internal surface of the cavity in the resurfacing shell 16. The viscosity of the cement 26 is such that the cement is self supporting when applied to the prepared head of the bone, so that it does not tend to fall off the surface after application and before the resurfacing shell 16 is applied. Techniques for applying such high viscosity cements are known, often involving manual application.

For secure fixation of the resurfacing shell 16 on to the prepared bone 14, it is preferred that the high viscosity bone cement 26 should penetrate the porous bone tissue of the head 12, as shown at 28 in FIG. 1. This can be achieved by applying pressure to the bone cement 26 before it cures. It is preferred that the bone cement 26 should penetrate the surface of the head 12 in the side surface regions 22, 23 as well as the top surface region 18.

It is also desirable that the thickness of mantle of cement 26 on the surface of the bone 14 should be approximately uniform, in particular so that the amount of the cement on the surfaces 22, 23 surrounding the axis 20 of the bone 14 is not significantly greater than a predetermined thickness (generally about 1 mm). It is also desirable that the amount of cement 26 on the side surfaces 22, 23 of the prepared bone 14 should not be significantly less than a predetermined thickness (generally about 1 mm).

Figures 2, 3:
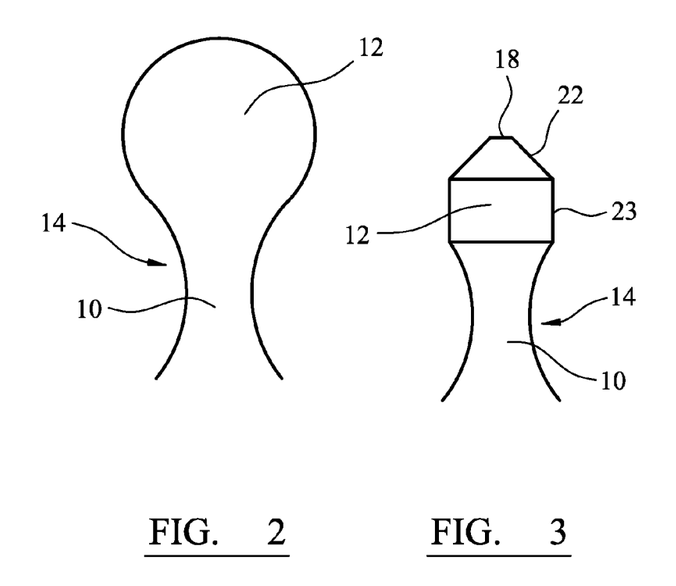
FIGS. 2 to 4 illustrate steps in a method of fitting the resurfacing shell to the femoral head shown in FIG. 1.

FIG. 2 shows the head 12 and neck 10 region of the femur 14 before bone tissue is resected. FIG. 3 shows the head 12 after it has been resected for example using a reamer (not shown) of the type disclosed in WO-2004/032767, to form the generally planar top surface 18 and side surfaces 22 and 23.

Figure 4:
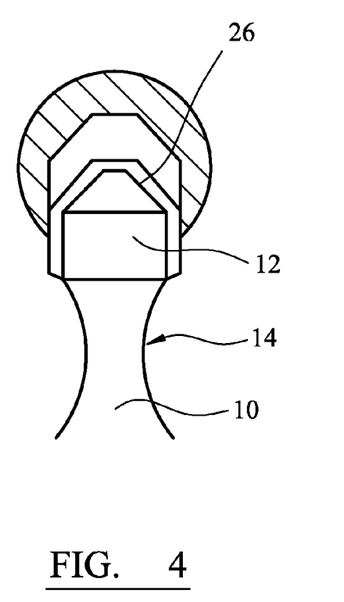

FIG. 4 shows the head 12 with the mantle of high viscosity bone cement 26 such as that sold by DePuy CMW under the trade mark SmartSet GHV formed around it, prior to the resurfacing shell 16 being fitted over the head. The bone cement 26 is applied to the head 12 of the bone manually by finger packing or by use of a syringe system. The bone cement 26 has a dough like consistency and is self supporting. The viscosity of the bone cement 26 can be measured using a viscometer. An example of a suitable instrument is that available under the trade name Brookfield RVDV-III. The temperature of the reactive bone cement components is 23° C. prior to mixing. The bone cement components are thoroughly mixed before the measurements are taken. The viscosity of the bone cement is at least $10^6$ cp.

Figure 5:
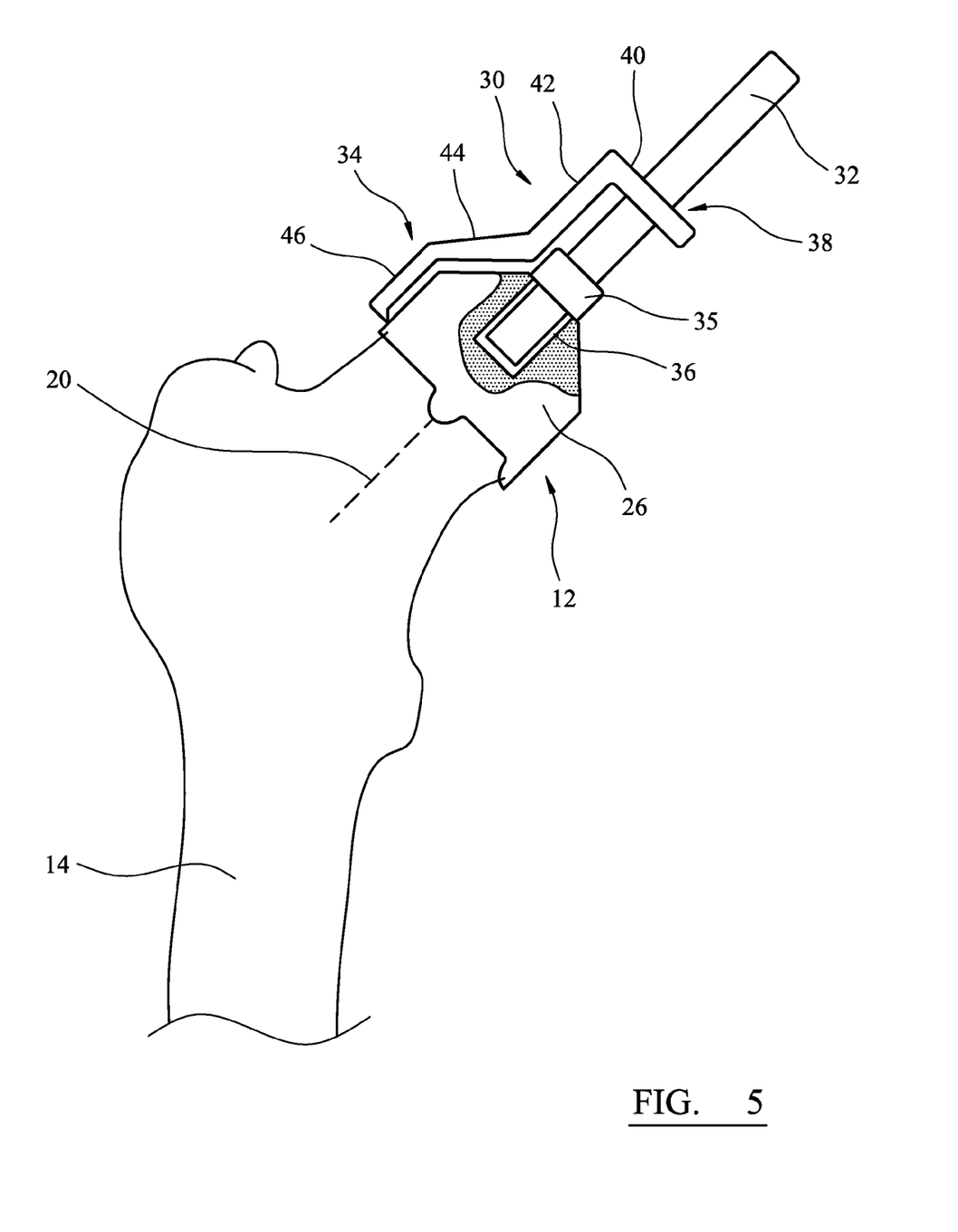
FIG. 5 is a front view of part of the femur shown in FIG. 1, the femur shown during a resurfacing procedure utilising an instrument for controlling the distribution of bone cement on the surface of the head of the femur, according to an embodiment of the present invention.

Referring now to FIG. 5, the femur 14 is shown in greater detail and at a stage in a procedure for applying the resurfacing shell 16 shown in FIG. 1 to the head 12, using an instrument 30 in accordance with an embodiment with the present invention. The instrument 30 serves for controlling the distribution of bone cement on the surfaces 18, 22 and 23 of the head 12 of the femur 14, to prepare the femur 14 to receive the resurfacing prosthesis, which takes the form of the resurfacing shell 16. The instrument 30 generally comprises a shaft 32 which is coupled to the femur 14 and an arm 34 coupled to the shaft 32. The arm 34 can be rotated about the head 12 of the femur 14. The arm is shaped so as to contact cement 26 on the head 12 of the femur 14 in a sweeping action when the arm 34 is rotated about the head 12. This rotation of the arm 34 about the femur head 12 removes excess cement applied to the head 12 to form a cement mantle, typically having a thickness of about 1.25 mm. Accordingly, following use of the instrument 30, a cement mantle of desired thickness and even spread around the surfaces 22 and 23 of the femur head 12 is obtained, ensuring that a good fit is provided with the resurfacing shell 16 which is to be subsequently applied. Additionally, use of the instrument 30 assists in avoiding the various disadvantages associated with known techniques employing low viscosity cements by providing such an even and relatively uniform thickness cement mantle.

The structure of the instrument 30 and its method of operation will now be described in more detail. The shaft 32 is generally cylindrical and is located in an axial cavity 36 formed in the head 12 of the femur 14. The shaft 32 is dimensioned so as to be a tight interference fit in the cavity 36 such that rotation of the shaft 32 within the cavity is resisted. The shaft 32 also carries a depth stop 35 which abuts the surface 18 of the femur 14, limiting the extent of travel of the shaft 32 into the cavity 36 to thereby accurately locate the arm 34 relative to the surfaces 22 and 23. The depth stop also restricts undesired movement of the shaft 32 when the arm 34 is rotated, to assist in maintaining a desired clearance between the arm 34 and the head 12.

The arm 34 is rotatably coupled to the shaft 32 via a bearing assembly 38. The arm 34 includes a base portion 40 housing the bearing assembly 38, a main portion 42 extending from the base portion 40 in a direction parallel to the bone axis 20, an inclined portion 44 and a tip portion 46. The inclined portion 44 and tip portion 46 are each shaped to correspond to the respective surfaces 22 and 23 formed on the head 12 of the femur 14 described above, each defining a preferred clearance of about 1.5 mm, to define the desired thickness of cement mantle.

Typically the head 12 of the femur 14 is first reamed to the desired shape and the axial cavity 36 drilled to the desired depth. Cement is then applied to the surfaces 22 and 23 of the head 12, being careful to avoid passage of cement into the cavity 36. This may be achieved by fitting a temporary plug (not shown) in the cavity 36 prior to cement application. The shaft 32 is then located in the cavity 36 with the arm 34 positioned as shown in FIG. 5 and, with the shaft 32 securely located in the cavity 36, the arm 34 is rotated a full 360 E turn around the head 12 of the femur 14, typically in a single rotational direction. During passage of the arm 34, excess cement is scraped from the surfaces 22 and 23 of the head 12, and the arm 34 exerts a force on the cement, thereby urging the cement into the pores of the cancellous bone 28 in the head 12 of the femur 14.

After a full turn of the arm 34 has been completed, the shaft 32 is carefully removed from the cavity 36, carrying the arm 34 away from the head 12, and with the excess cement removed by the arm 34 during rotation remaining on the arm. If desired, a layer of cement is then applied manually to portions of the surface 18 of the head 12 surrounding the cavity 36, although these portions, which may be relatively small depending on the diameter of the cavity 36, are typically left bare. The femur head 12 is now ready for application of the resurfacing shell 16, which is firmly pressed onto the head 12 according to known techniques, and as shown in FIG. 1. Where the portions of the surface 18 surrounding the cavity 36 are left bare, application of the shell 16 to the head 12 typically extrudes cement from the surface 22 on to the surface 18, to provide a good bond in the polar region of the shell. After curing of the cement the resurfaced femur 14 is then ready for mating with a corresponding socket component in the acetabulum (not shown), in a fashion known in the art.

Typically the arm 34 is of a relatively rigid plastics material, but may alternatively be of a metal or a metal alloy. In a variation on the illustrated embodiment, the arm 34 may carry a wiper portion (not shown) for contacting the cement 26, the wiper portion being more flexible than a remainder of the arm. The wiper portion may be relatively flexible/elastically deformable, to assist in urging the cement 26 into the porous bone tissue 28, and may be provided as a coating or sheet of material provided on an internal surface of the arm 34.

Figure 5A:
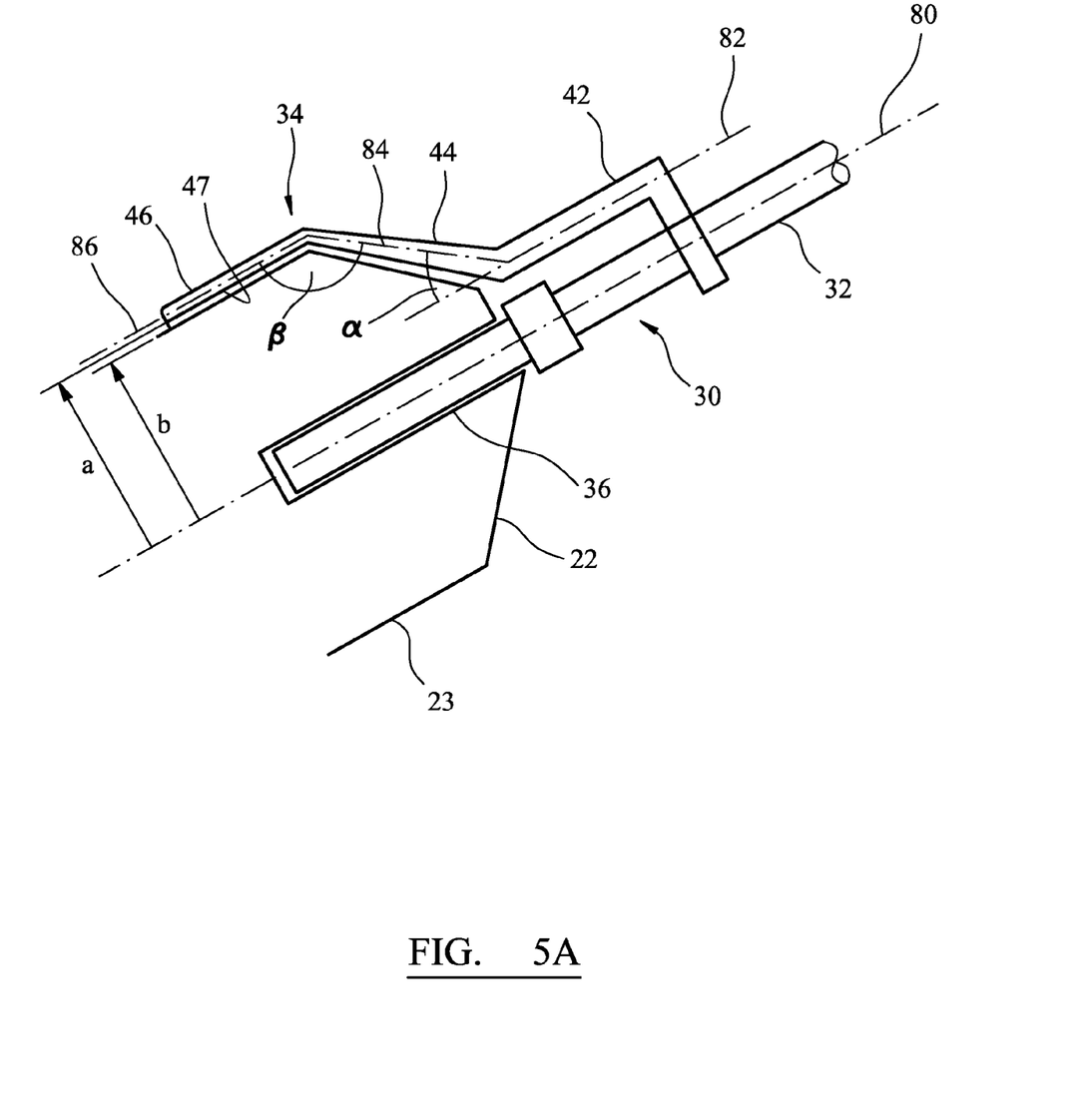
FIG. 5A is a view of the instrument for controlling the distribution of bone cement shown in FIG. 5, illustrating certain dimensions and angles of the instrument.

Turning now to FIG. 5A, there is shown a view of the instrument 30 of FIG. 5 illustrating certain dimensions and angles of the instrument. In the Figure, a main longitudinal axis of the shaft 32 is shown and is given the reference numeral 80. When the shaft 32 is located in the cavity 36, the axis 80 is coaxial to an axis of the cavity.

The main, inclined and tip portions 42, 44 and 46 of the arm 34 have respective main axes 82, 84 and 86. An angle α between the axis 82 of the main portion 42 and the axis 84 of the inclined portion 44 is typically around 45°, but may be some other suitable angle. For example, the angle may be at least about 30°, and may be in the range of between about 45° and about 85°. The angle selected will depend upon factors including the corresponding angle of the prepared side surface 22 of the head 12 of the bone.

Typically and as described above, the side surface 23 of the prepared head 12 of the bone will be inclined (tapered) by around 3°. The tip portion 46 of the arm 34 is arranged such that the axis 86 is inclined at a corresponding angle of around 3° relative to the main axis 80 of the shaft 32. Once again, other angles may be selected and the angle may be between about 3° and about 15°. An angle β between the axis 86 of the tip portion 46 and the axis 84 of the inclined portion 44 will be selected according to the taper of the surface 23 which the tip portion 46 is required to accommodate. If the side surface 23 was disposed parallel to the main axis 80 of the shaft, then the angle β would be the internal angle corresponding to the external angle α. Thus where the angle α is 45°, the angle β will be 135°. In the illustrated embodiment, the side surface 23 has a 3° taper, therefore the angle β is 138°.

When the arm 34 is rotated about the head 12 of the bone, the arm 34 follows a circumferential path. The diameter of this circumferentially extending path is defined by an internal surface 47 of the tip portion 46. Taking account of the fact that the tip portion axis 86 is typically inclined at an angle to the main axis 80 of the shaft 32, this diameter will increase in a direction away from the intersection between the arm portions 44 and 46. A radial distance a (shown in the Figure) from the axis 80 to the internal surface 47 would typically around 2 cm, accounting of course for the above variations due to the taper of the side surface 23. Ultimately this dimension 'a' is dependent upon the clearance required between the internal surface 47 of the tip portion 46 and the surface 23 of the prepared head. A typical range of dimensions for the distance 'a' will be about 1.5 to about 3 cm. Also, a ratio of the distance 'a' relative to a distance 'b' (which is the radial width of the prepared head 12 of the bone) will typically be in the range 1.05:1 to 1.2:1, thereby providing a clearance in the range of 0.5 to 2 mm between the surfaces 47 and 23.

A length of the inclined portion 44 of the arm 34 will once again be dependent on factors including the radial dimension 'b' of the prepared head 12 of the bone, and also the angle of incline of the side surface 22. However, for typical dimensions of prepared bone heads, the inclined portion 44 may have a length of around 3 cm, but could be in the range of at least about 2 cm to no more than about 5 cm.

Figure 6:
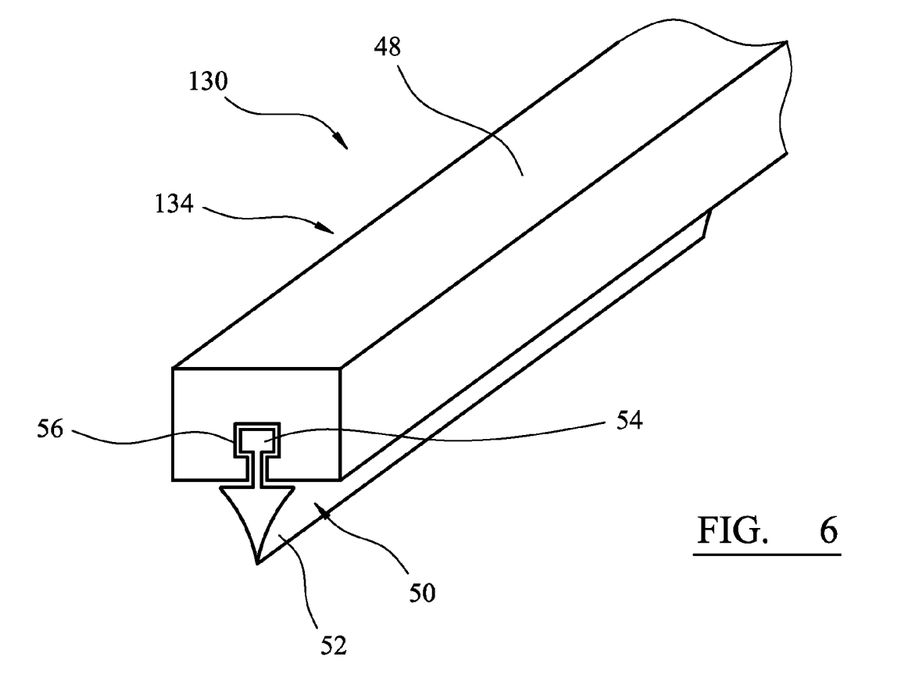
FIG. 6 is a perspective view of part of an instrument for controlling the distribution of bone cement on the surface of a head of a femur, according to an alternative embodiment of the present invention.

Turning now to FIG. 6, there is shown a perspective view of part of an instrument for controlling the distribution of bone cement on the surface of a prepared head of a bone, in accordance with an alternative embodiment of the present invention, the instrument indicated generally by reference numeral 130. Like components of the instrument 130 with the instrument 30 of FIG. 5 share the same reference numerals, incremented by 100.

The instrument 130 is in fact of the same construction as the instrument 30 and operated in a similar fashion, save that an arm 134 of the instrument 130 comprises a support portion 48 and a wiper portion 50 mounted on the support portion 48. The wiper portion 50 is of a material having a lower Shore hardness than that of the support portion, and is relatively flexible. Suitable materials for the wiper portion 50 will typically have a Shore hardness in the range of 10 to 60. Appropriate materials include silicone rubbers, particularly medical grade silicone rubbers having a Shore hardness of, for example, 10, 15, 20, 40 or 60. Such silicone rubber materials are commercially available from various manufacturers including Primasil Silicones Ltd. in the United Kingdom.

The wiper portion 50 comprises a tapered blade 52 which contacts cement on a head of a prepared bone, and a locating strip 54 shaped to engage in a channel 56 formed in the support portion 48 in a sliding fit. This sliding mounting of the wiper portion 50 in the support portion 48 permits easy replacement of the wiper portion 50 should it become degraded through repeated use.

When the arm 134 is rotated about a head of a bone, such as the head 12 of the femur 14 shown in FIG. 1, the tapered blade 52 is elastically deformed and deflected away from the surface of the femoral head 12. This deformation of the blade 52 assists in urging the cement into the porous bone tissue 28. A suitable material for the wiper portion 50 is a silicone rubber or elastomeric material having a Shore hardness of between about 10 and 100, in particular having a Shore hardness in the range 25 to 70.

Figure 7:
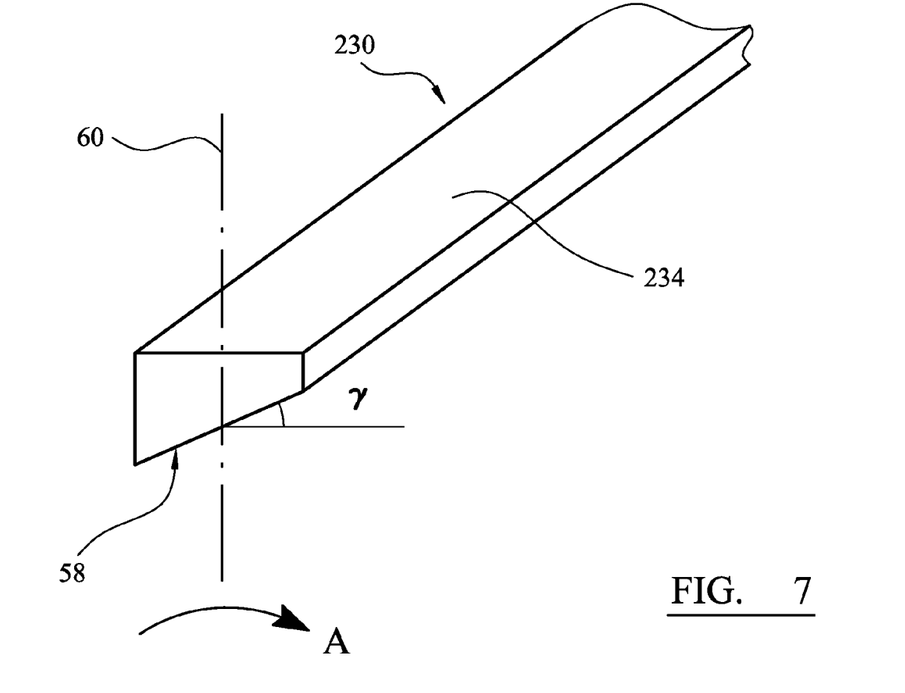
FIG. 7 is a perspective view of part of an instrument for controlling the distribution of bone cement on the surface of a head of a femur, according to a further alternative embodiment of the present invention.

Turning now to FIG. 7, there is shown a perspective view of part of an instrument for controlling the distribution of bone cement on the surface of a prepared head of a bone, in accordance with a further alternative embodiment of the present invention, the instrument indicated generally by reference numeral 230. Like components of the instrument 230 with the instrument 30 of FIG. 5 share the same reference numerals, incremented by 200.

The instrument 230 is in fact of the same construction as the instrument 30 and operated in a similar fashion, save that an arm 234 of the instrument 230 has an internal surface 58 which is inclined at an angle γ relative to a radius 60 of the shaft 58. Also, providing the arm 234 with such an inclined internal surface 58 requires the arm 234 to be rotated in about a head of a bone in a specific rotational direction, as indicated by the arrow A.

Typically the angle γ will be at least 45°, but may be larger or smaller depending upon factors including the viscosity of the bone cement to be applied to the head of the bone in question. In a similar fashion to the flexible wiper portion 50 of the instrument 130, the inclined surface 58 assists in urging the cement into the porous bone tissue of a bone, such as the tissue 28 of the head 12 of the femur 14 shown in FIG. 1.

Figure 8:
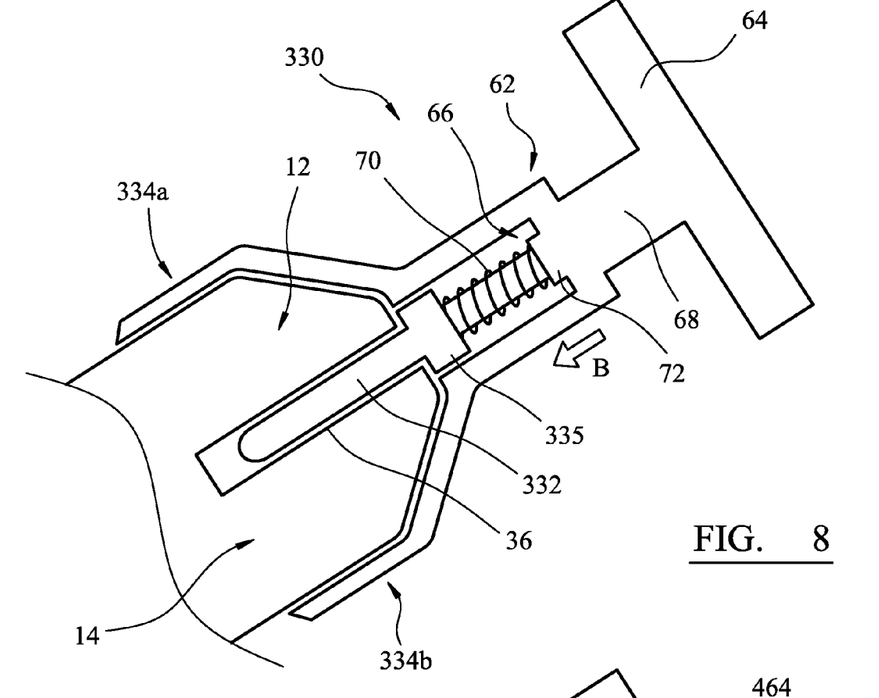
FIG. 8 is a front view of an instrument for controlling the distribution of bone cement on the surface of a head of a femur, according to a yet further alternative embodiment of the present invention.

Turning now to FIG. 8, there is shown a front view of an instrument for controlling the distribution of bone cement on the surface of a prepared head of a femur, according to a yet further alternative embodiment of the present invention, the instrument indicated generally by reference numeral 330 and shown in use during a resurfacing procedure. Like components of the instrument 330 with the instrument 30 of FIG. 5 share the same reference numerals, incremented by 300.

The instrument 330 is of similar construction to the instrument 30 and operated in a similar fashion. However, the instrument 330 includes a shaft 332 which is located in an axial cavity of a head of a femur, such as the cavity 36 in the head 12 of the femur 14 shown in FIG. 1. In a similar fashion to the shaft 32 of instrument 30, the shaft 332 carries a depth stop 335 which restricts passage of the shaft into the cavity 36. The instrument 330 includes two arms 334a and 334b which are rotatable about the head 12 in unison. This is achieved by providing the arms 334a, 334b as part of an arm assembly 62 including a handle 64, and rotatably mounting the arm assembly 62 on the shaft 332. The arm assembly 62 is rotatably mounted on the shaft 332 by locating an upper end 66 of the shaft 332 in a passage (not shown) in a body portion 68 of the arm assembly 62.

The arm assembly 62 is coupled to the shaft 332 in a fashion which permits limited axial movement of the arm assembly 62 relative to the shaft 332, and thus which permits movement of the arms 334a and 334b towards the head 12 of the femur 14 in the direction of the arrow B of FIG. 8. A spring 70 is mounted around a portion of the shaft 332 between the depth stop 335 and a boss 72 of the body portion 68, and biases the arm assembly 62 in a direction away from the depth stop 335. In this fashion, when the shaft 332 has been located in the cavity 36, it is necessary for a user to press the arm assembly 62 down on to the head 12 whilst rotating the arms 334a, 334b using the handle 64. Providing the instrument 330 with such a spring 70, thereby permitting adjustment of a distance between the arm assembly 62 and the depth stop 335, facilitates transmission of a force to cement 26 on the femur head 12 to urge the cement into the porous bone tissue 28.

The arm assembly 62 is restricted against release from the shaft through 32 by a flange (not shown) provided on the end 66 of the shaft 332, which locates within the passage in the body portion 68 and which is engaged by a restraint (not shown) in the boss 72. This restricts passage of the flange past the boss. Furthermore, the dimensions of the passage in the body portion 68 are selected so as to limit the extent of travel of the arm assembly 62 towards the depth stop 335, to thereby restrict movement of the arms 334a, 334b towards the head 12. This thereby permits control of a minimum clearance between internal surfaces of the arms 334a, 334b and the head 12, and thus the thickness of a mantle of bone cement 26 formed when the arms are rotated (typically around 1 mm). However, in a variation, a spacer (not shown) such as collar may be located around the spring 70 to restrict travel of the arm assembly 62.

Figure 9:
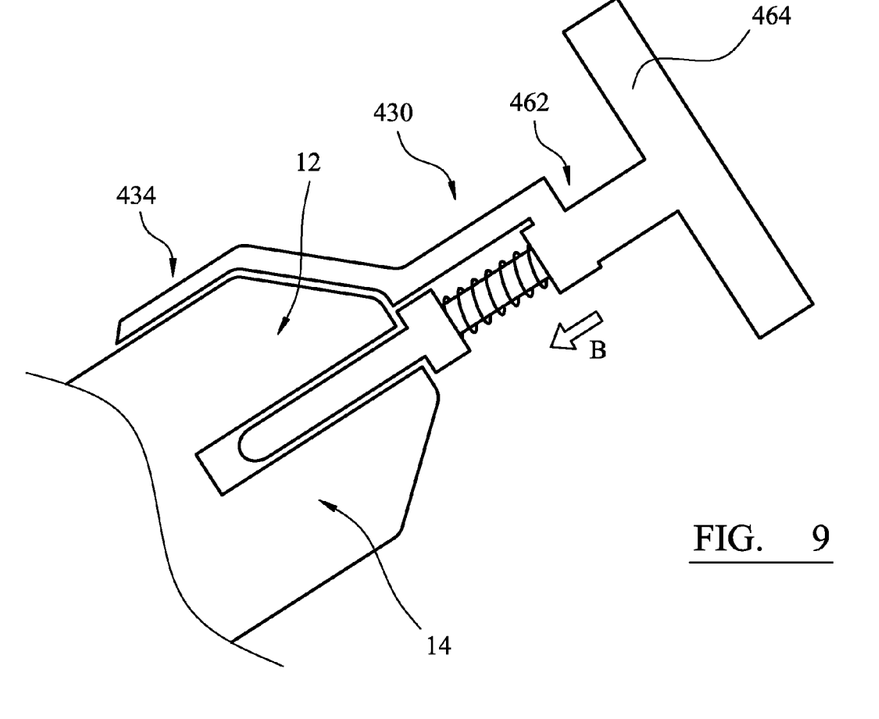
FIG. 9 is a front view of an instrument for controlling the distribution of bone cement on the surface of a prepared head of a femur, according to a still further alternative embodiment of the present invention.

Turning now to FIG. 9, there is shown a front view of an instrument for controlling the distribution of bone cement on the surface of a prepared head of a femur, in accordance with a still further alternative embodiment of the present invention, the instrument indicated generally by reference numeral 430. The instrument 430 is shown in use during a resurfacing procedure, and like components of the instrument 430 with the instruments described above share the same reference numerals, incremented by 400.

The instrument 430 is shown during a resurfacing procedure on the head 12 of the femur 14 of FIG. 1, and is in fact of similar construction to the instrument 330 of FIG. 8, save that the instrument 430 includes an arm assembly 462 having only a single arm 434. The instrument 430 is therefore operated in a similar fashion to the instrument 330, by exerting a force on the arm assembly 462 to urge the arm 434 in the direction of the arrow B, the arm 434 rotated about the head 12 of the femur 14 by turning a handle 464.

Figures 10, 11, 12:
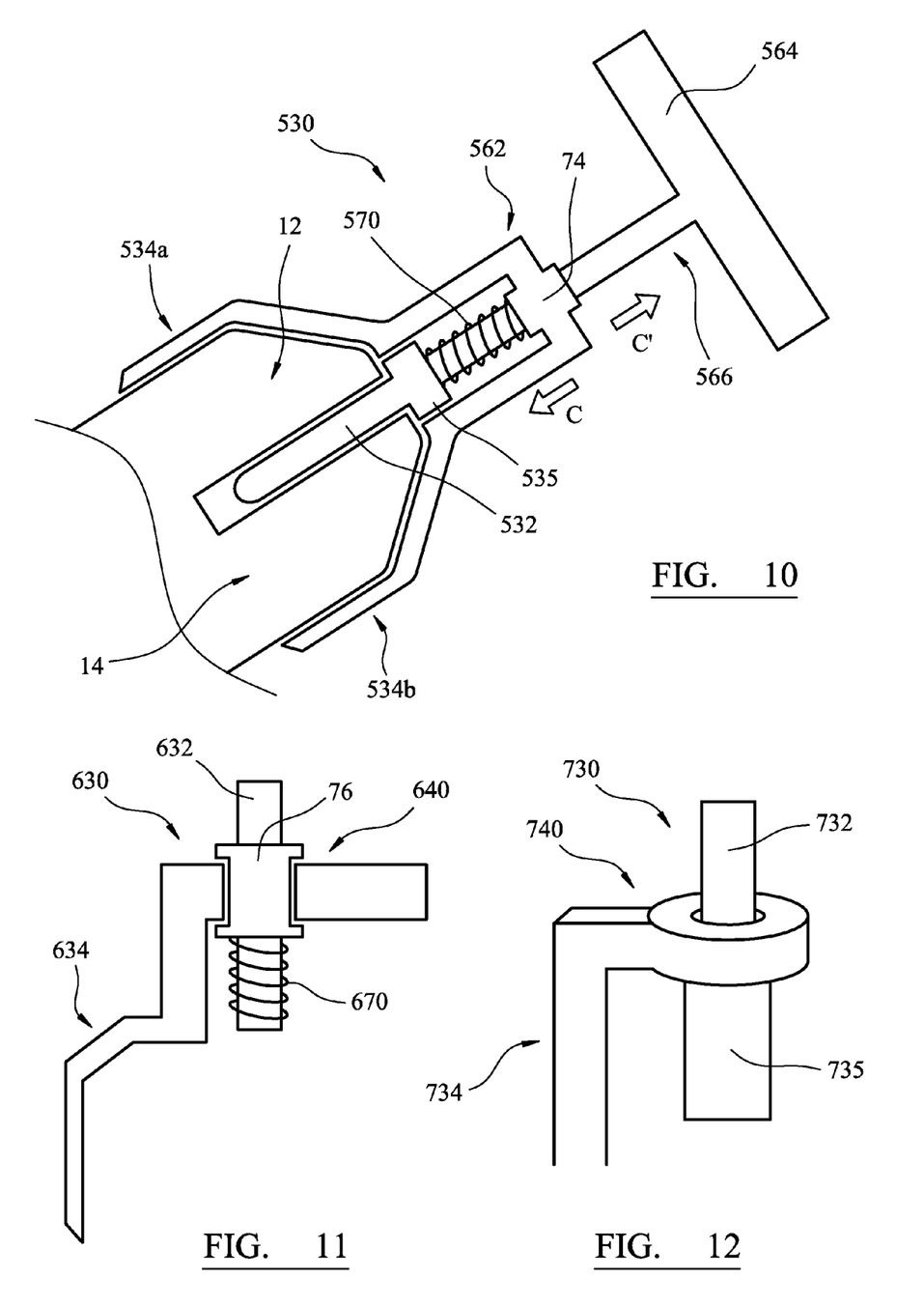
FIG. 10 is a front view of an instrument for controlling the distribution of bone cement on the surface of a prepared head of a femur, according to a still further alternative embodiment of the present invention.
FIG. 11 is a front view of part of an instrument for controlling the distribution of bone cement on the surface of a prepared head of a femur, according to a still further alternative embodiment of the present invention.
FIG. 12 is a schematic view of part of an instrument for controlling the distribution of bone cement on the surface of a prepared head of a femur, in accordance with a still further alternative embodiment of the present invention.

Turning now to FIG. 10, there is shown a front view of an instrument for controlling the distribution of bone cement on the surface of a prepared head of a bone according to a yet further alternative embodiment of the present invention, the instrument indicated generally by reference numeral 530. Like components of the instrument 530 with the instruments described above share the same reference numerals incremented by 500.

The instrument 530 includes an arm assembly 562 having two arms 534a, 534b, in a similar fashion to the instrument 330 of FIG. 8, and is shown during a resurfacing procedure on the head 12 of the femur 14 of FIG. 1. The arm assembly 562 includes a collar 74 from which the arms 534a, 534b extend, and the collar 74 is mounted on a shaft 532 of the instrument 530. The shaft 532 carries a depth stop 535, and a handle 564 is provided at an end 566 of the shaft 532. The collar 74 is slidably mounted on the shaft 532 and can move in the direction of the arrows C-C' of FIG. 10. However, a spring 570 is mounted on the shaft 532 between the depth stop 535 and the collar 74, restricting movement of the arm assembly 562, and thus the arms 534a and 534b, in the direction of the arrow C (towards the head 12).

The clearance between internal surfaces of the arms 534a, 534b is therefore controlled by an operator according to the force applied on the arm assembly 562. The spring 570 may therefore be selected to have a spring force which is sufficiently great so as to restrict further movement of the arm assembly 562 in the direction C once an ideal clearance, typically no smaller than 1 mm, is achieved. However, control of the extent of movement of the arm assembly 562 towards the head 12 may be achieved by providing a spacer around the spring 570. Operation of the instrument 530 is otherwise as described in relation to the instrument 330 of FIG. 8, save that the arms 534a, 534b are rotated about the head 12 by directly gripping one or both of the arms.

Turning now to FIG. 11, there is shown a schematic view of part of an instrument for controlling the distribution of bone cement on the surface of a prepared head of a femur, in accordance with a yet further alternative embodiment of the present invention, the instrument indicated generally by reference numeral 630. Like components of the instrument 630 with the instruments described above share the same reference numerals, incremented by 600.

The instrument 630 is of similar construction to the instrument 30 of FIG. 5, save that it includes a spring 670 located between a depth stop (not shown) and a bearing 76 provided in a base portion 640 of an arm 634 of the instrument. The spring 670 acts to bias the arm 634 away from a head of a femur, such as the head 12 of the femur 14 shown in FIG. 1, in a similar fashion to the spring 70 of the instrument 330 of FIG. 8. The bearing 76 typically takes the form of a hollow cylinder of a low friction plastics material such as PTFE. The bearing 76 is secured to the base portion 640, and can both slide along and rotate about a shaft 632 of the instrument 630. This permits the arm 634 to be urged towards and rotated about the head 12 of the femur 14. In a variation, the bearing 76 may comprise a conventional roller or needle type bearing. It will be understood that the mounting arrangement of the arm 634 on the shaft 632 may be applied to one or more of the other instruments described herein.

Turning now to FIG. 12, there is shown a schematic view of an instrument for controlling the distribution of bone cement on the surface of a prepared head of a bone, in accordance with a yet further alternative embodiment of the present invention, the instrument indicated generally by reference numeral 730. Like components of the instrument 730 with the instruments described above share the same reference numerals, incremented by 700.

The instrument 730 is similar to the instrument 30 of FIG. 5 in construction and operation. However, a shaft 732 of the instrument 730 includes a lower portion defining a depth stop 735 for restricting passage of the shaft 732 into a cavity in a head of a femur, such as the cavity 36 in the head 12 of the femur 14 shown in FIG. 1. An arm 734 of the instrument 730 includes a base portion 740 which is mounted around a portion of the shaft 732 above the depth stop 735, and the base portion 740 typically carries a bearing (not shown) similar to the bearing 76 shown in FIG. 11, to permit axial and rotational movement of the arm 734 about the shaft 732. Additionally however, the depth stop 735 defines a ledge (not shown) which restricts movement of the arm 734 towards the head 12 of the femur 14 and thus the thickness of the cement mantle. As with the instrument 630 of FIG. 11, it will be understood that the mounting arrangement of the arm 734 on the shaft 732 may be applied to one or more of the other instruments described herein.

The cavity in the head of the bone may be tapered, typically at around 3 E from an axis of the cavity, and the shaft of the instrument may have a corresponding taper. In this fashion, passage of the shaft into the cavity may be restricted by abutment between the internal wall of the cavity and the outer surface of the shaft. This may control the maximum clearance between an internal surface of the arm and the head of the bone, and thus the thickness of the cement mantle formed.

One or more features of the instruments described above may be provided in combination in an instrument according to a further embodiment of the present invention.

The shaft of the instrument may be mounted for rotation relative to the head of the femur and the arm secured to the shaft such that rotation of the shaft produces a corresponding rotation of the arm about the head of the femur. This may be achieved either by rotatably mounting the shaft within a cavity formed in the head of the femur, or by providing the shaft with a first portion secured to the femur and a second portion which is rotatable relative to the first portion, the second portion carrying the arm and thus being rotatable about the head of the femur together with the second portion of the shaft.

The arm may be articulated, and may comprise a plurality of arm portions, which portions may be hinged or otherwise pivotally coupled.

The arm may be releasably coupled to the shaft, and in embodiments of the invention, a plurality of arms of different shapes and/or dimensions may be provided, each arm shaped to correspond to a head of a femur which has been reamed or otherwise formed into a desired shape.

I claim:

1. An instrument for controlling the distribution of bone cement on a surface of a prepared bone, the bone having a bore and cement disposed on at least a portion of the bone, the instrument comprising:
   a shaft having a shaft axis, the shaft configured to be at least partially disposed within the bore of the bone; and
   at least one arm rotatably coupled to the shaft such that the at least one arm rotates about the shaft axis, the at least one arm comprises a support portion and at least one wiper portion mounted on the support portion, the wiper portion comprises a material that is more flexible than a material of the support portion, and wherein the wiper portion is shaped to contact the cement on the bone when the at least one arm is rotated about the shaft axis.

2. The instrument of claim 1, wherein the material of the wiper portion has a Shore hardness of at least about 10 and not more than about 100.

3. The instrument of claim 2, wherein the material of the wiper portion has a Shore hardness of at least about 15 and not more than about 70.

4. The instrument of claim 1, wherein the at least one arm comprises an internal surface that contacts the cement on the bone, and wherein an angle between at least a part of the internal surface of the at least one arm and a radius extending from the shaft axis is at least about 10 degrees.

5. The instrument of claim 4, wherein the angle is at least about 45 degrees.

6. The instrument of claim 1, wherein the shaft has a distal end and is releasably secured to the bone such that the shaft extends from the head of the bone when the distal end is disposed within the bore.

7. The instrument of claim 1, wherein the at least one arm is releasably coupled to the shaft.

8. The instrument of claim 1, wherein the shaft comprises a first portion that is releasably secured to the bone, and a second portion that is coupled to the at least one arm, and wherein the second portion is rotatable relative to the first portion.

9. The instrument of claim 1, wherein the at least one arm comprises a plurality of arm portions.

10. The instrument of claim 1, comprising a depth stop disposed on the shaft having a dimension larger than the bore of the bone.

11. The instrument of claim 1, wherein the at least one arm is axially movable relative to the shaft.

12. The instrument of claim 11, comprising a spring disposed on the shaft.

13. An instrument for controlling the distribution of bone cement on a surface of a prepared bone, the bone having a bore and cement disposed on at least a portion of the bone, the instrument comprising:
- a shaft having a shaft axis, the shaft configured to be at least partially disposed within the bore of the bone;
- at least one arm rotatably coupled to the shaft such that the at least one arm rotates about the shaft axis, the at least one arm shaped so as to contact the cement on the bone when the at least one arm is rotated about the shaft axis, the at least one arm being axially movable relative to the shaft;
- a depth stop integral with the shaft, the depth stop having a dimension larger than the bore of the bone; and
- a spring disposed on the shaft, wherein the spring is located between the depth stop and the at least one arm.

14. A kit of parts to be assembled to form an instrument for controlling the distribution of bone cement on a surface of a prepared bone, the bone having a bore and cement disposed on at least a portion of the bone, the instrument comprising:
- a shaft having a shaft axis, the shaft configured to be at least partially disposed within the bone;
- a first arm rotatably coupled to the shaft such that the first arm rotates about the shaft axis, wherein the first arm comprises a first support portion and at least one wiper portion mounted on the first support portion, and wherein the at least one wiper portion contacts the cement on the bone when the first arm is rotated about the shaft axis, and wherein the at least one wiper portion comprises a material that is more flexible than a material of the support portion;
- a second arm rotatably coupled to the shaft such that the second arm rotates about the shaft axis, the second arm shaped so as to contact the cement on the bone when the second arm is rotated about the bone, wherein the second arm comprises a second support portion and at least one wiper portion mounted on the second support portion, and wherein the at least one wiper portion contacts the cement on the bone when the second arm is rotated about the shaft axis, and wherein the at least one wiper portion comprises a material that is more flexible than a material of the support portion; and
- wherein the first arm has a different cross-sectional shape than the second arm.

15. A method of controlling the distribution of bone cement on a surface of a prepared bone, the bone having a bore and cement disposed on at least a portion of the bone, comprising the steps of:
- disposing a shaft having a shaft axis within the bore of the bone, the shaft having at least one arm rotatably coupled thereto such that the at least one arm rotates about the shaft axis, the at least one arm comprises a support portion and at least one wiper portion mounted on the support portion, the wiper portion comprises a material that is more flexible than a material of the support portion; and
- rotating the at least one arm about the shaft axis thereby causing the wiper portion to contact the cement on the bone.

* * * * *